United States Patent
Tuberquia et al.

(10) Patent No.: US 11,098,144 B2
(45) Date of Patent: Aug. 24, 2021

(54) ETHYLENE/ALPHA-OLEFIN/POLYENE INTERPOLYMERS AND COMPOSITIONS CONTAINING THE SAME

(71) Applicant: Dow Global Technologies LLC, Midland, MI (US)

(72) Inventors: Juan C. Tuberquia, Manvel, TX (US); Colin LiPiShan, Pearland, TX (US); Zhe Zhou, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 74 days.

(21) Appl. No.: 16/314,283

(22) PCT Filed: Jun. 30, 2017

(86) PCT No.: PCT/US2017/040207
§ 371 (c)(1),
(2) Date: Dec. 28, 2018

(87) PCT Pub. No.: WO2018/005922
PCT Pub. Date: Jan. 4, 2018

(65) Prior Publication Data
US 2019/0225724 A1   Jul. 25, 2019

Related U.S. Application Data

(60) Provisional application No. 62/357,041, filed on Jun. 30, 2016.

(51) Int. Cl.
C08F 210/18 (2006.01)
G01N 33/44 (2006.01)
G01N 24/08 (2006.01)

(52) U.S. Cl.
CPC ......... C08F 210/18 (2013.01); G01N 24/087 (2013.01); G01N 33/442 (2013.01); *C08F 2800/20* (2013.01); *C08F 2810/20* (2013.01)

(58) Field of Classification Search
CPC .............. C08F 210/18; C08F 2800/20; C08F 2810/20; G01N 33/442; G01N 24/087
See application file for complete search history.

(56) References Cited

U.S. PATENT DOCUMENTS

| 5,610,254 | A  | 3/1997  | Sagane et al. |
|-----------|----|---------|---------------|
| 6,225,427 | B1 | 5/2001  | Burton et al. |
| 6,680,361 | B1 | 1/2004  | Cady et al. |
| 6,723,794 | B2 | 4/2004  | Kawasaki et al. |
| 8,178,031 | B2 | 5/2012  | Jacob et al. |
| 8,299,189 | B2 | 10/2012 | Boone et al. |
| 8,765,834 | B2 | 7/2014  | Jacob |
| 9,029,487 | B2 | 5/2015  | Klosin et al. |
| 9,102,824 | B2 | 8/2015  | Liang et al. |
| 9,120,887 | B2 | 9/2015  | Voorheis et al. |
| 9,422,383 | B2 | 8/2016  | LiPiShan et al. |
| 2006/0183631 | A1 | 8/2006 | Lee et al. |
| 2008/0033124 | A1 | 2/2008 | Jiang et al. |
| 2013/0031611 | A1 | 1/2013 | Barreto |
| 2015/0274867 | A1 | 10/2015 | LiPiShan et al. |
| 2017/0354148 | A1 | 12/2017 | Degenhardt et al. |
| 2018/0105626 | A1 | 4/2018 | Fontaine et al. |
| 2018/0127564 | A1 | 5/2018 | LiPiShan et al. |
| 2018/0282597 | A1 | 10/2018 | LiPiShan et al. |
| 2019/0055422 | A1 | 2/2019 | Brennan et al. |

FOREIGN PATENT DOCUMENTS

| EP | 1433812 A1 | 6/2004 | |
|----|------------|--------|---|
| JP | 2004035813 A | 2/2004 | |
| WO | 2011/065877 A1 | 6/2011 | |
| WO | 2012/092491 A2 | 7/2012 | |
| WO | WO-2012092491 A2 * | 7/2012 | ............ C08L 47/00 |
| WO | 2017/206009 A1 | 12/2017 | |

OTHER PUBLICATIONS

Budzelaar, Computational Molecular Science, 2012, vol. 2, No. 2, p. 221-241.
Daslin, Macromolecules, 2015, vol. 48, No. 13, p. 4680-469.
PCT/US2017/040207, International Search Report and Written Opinion dated Jul. 12, 2017.
PCT/US2017/040207, International Preliminary Report on Patentability dated Oct. 1, 2019.

* cited by examiner

*Primary Examiner* — Robert D Harlan

(57) ABSTRACT

A composition comprising an ethylene/alpha-olefin/non-conjugated polyene, and wherein the ethylene/alpha-olefin/non-conjugated polyene comprises the following property: a "13C NMR % iCB Peak Area," which is the {[(13C NMR peak area from 34.4 ppm to 34.6 ppm) divided by (the 13C NMR sum integral area from 160.0 to 100.0 and from 60.0 ppm to 0.00 ppm)]×100}, that is >0.010%, as determined by 13C NMR.

20 Claims, 2 Drawing Sheets

ETHYLENE/ALPHA-OLEFIN/POLYENE INTERPOLYMERS AND COMPOSITIONS CONTAINING THE SAME

REFERENCE TO RELATED APPLICATIONS

This application claims the benefit of U.S. Provisional Application 62/357,041 filed Jun. 30, 2016, and incorporated herein by reference.

BACKGROUND OF THE INVENTION

There is a need for new compositions containing ethylene/alpha-olefin/non-conjugated polyene interpolymers that can be used for vulcanized rubber compositions, and provide improved mixing and processability, improved mechanical properties, and improved product consistency. One of the variables used to tailor the rheological behavior of polymer molecules is via the introduction of long chain branches (LCB) that have comparable length to that of the backbone. The more of these branches are introduced into the backbone (typically estimated by GPC), the higher the viscosity at low shear rates (V0.1) and shear thinning behavior exhibited by the polymer (rheology ratio, RR). Catalyst technology used today to make EPDM introduces long chain branches at a certain degree and has traditionally coupled high molecular weight polymers with high viscosities at low shear rates. However, there is a need for ethylene/alpha-olefin/nonconjugated polyene interpolymers that have a combination of low viscosities at high shear rates, expected from linear molecules, with the inherent tendency of catalysts to introduce branching, for improved rheology and mechanical properties.

WO 2007/136494 disclosed ethylene/alpha-olefin/diene polymers prepared from a catalyst composition comprising a zirconium complex of a polyvalent aryloxyether. WO 2006/009976 discloses processes for preparing polyolefins in the presence of a perfluorocarbon or hydrofluorocarbon with an activated, nonmetallocene, metal-centered, heteroaryl ligand catalyst. Polymers and compositions are also disclosed in the following: WO2012/027448, WO2013/096573, WO2014/084893, WO2011/008837, WO2012/092491, US20060183631, WO2011/163176, EP1433812A1, WO2011/041230, WO2006/009976, WO2000/26268, US8178031, EP751182A1, EP718324A1, WO2011/0065877, US2013/031611, JP04132672B2 (abstract), JP2004035813 (abstract), EP1433812A1, and PCT/US16/020212 (filed Mar. 1, 2016). However, as discussed above, there is a need for ethylene/alpha-olefin/nonconjugated polyene interpolymers that have a combination of low viscosities at high shear rates, expected from linear molecules, with the inherent tendency of catalysts to introduce branching, to provide improved mixing and processability and improved mechanical properties, and improved product consistency. This need has been met by the following invention.

SUMMARY OF THE INVENTION

A composition comprising an ethylene/alpha-olefin/non-conjugated polyene, and wherein the ethylene/alpha-olefin/non-conjugated polyene comprises the following property: a "13C NMR % iCB Peak Area," which is the {[(13C NMR peak area from 34.4 ppm to 34.6 ppm) divided by (the 13C NMR sum integral area from 160.0 to 100.0 and from 60.0 ppm to 0.00 ppm)]×100}, that is >0.010%, as determined by 13C NMR.

DETAILED DESCRIPTION OF THE INVENTION

Figure 1:
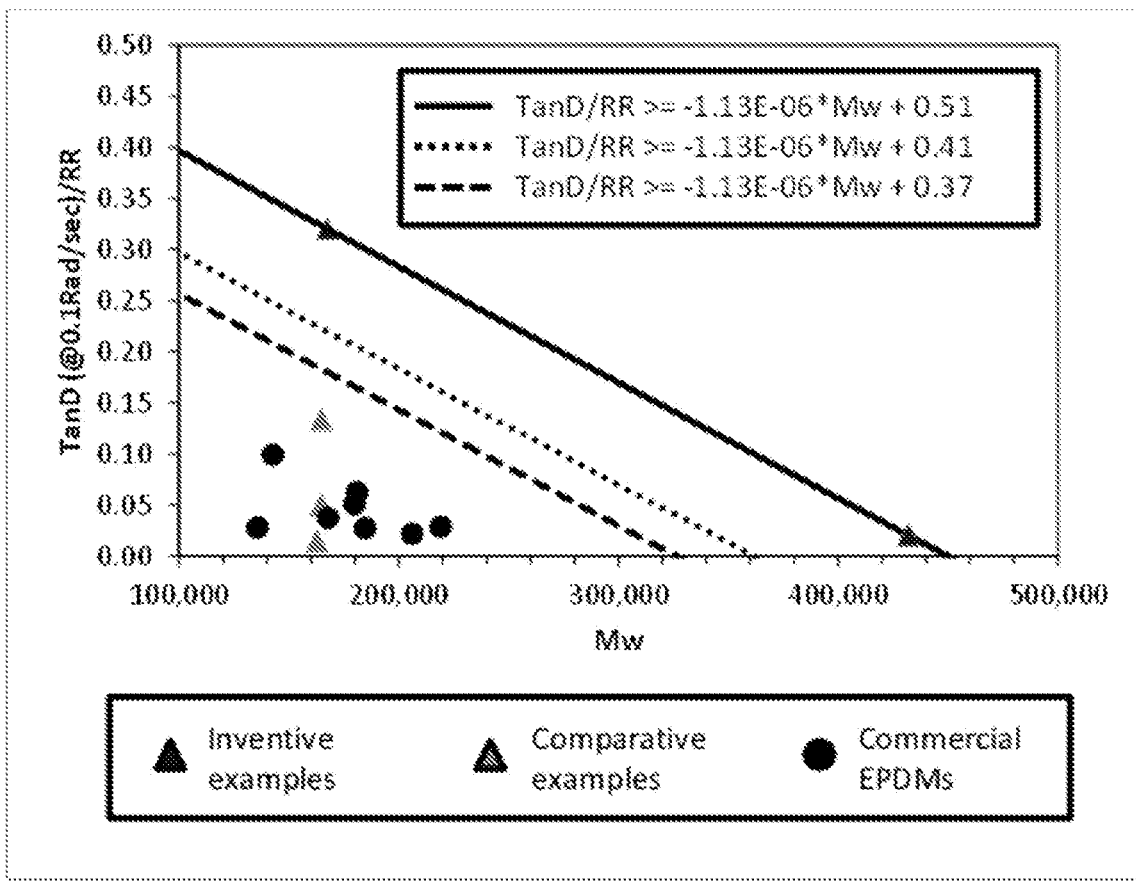
FIG. 1 depicts several "Tan D/RR versus Mw" plots, and this relationship for several inventive and comparative polymers (EPDMs).

It has been discovered a new polymer architecture using the concept of intermediate chain branching (iCB) in which oligomers produced in situ are rapidly incorporated into the polymer backbone. The branches resulting from incorporation of these oligomers do not increase the viscosity at low shear rates and therefore the resultant polymer exhibit similar behavior to that of linear molecules. Plus, incorporation is highly efficient such that oligomer content is very low or undetectable in the final polymer. It has been discovered that iCB in the inventive polymers. In the case of the iCB polymers reported here, the combination of high density of branches (estimated by NMR) and their intermediate length (30 to 75 carbon units) extend the backbone chain length required for entanglement in the molten state. This behavior is virtually similar to that of linear molecules.

It has been discovered a composition comprising an ethylene/alpha-olefin/non-conjugated polyene, and wherein the ethylene/alpha-olefin/non-conjugated polyene comprises the following property: a "13C NMR % iCB Peak Area," which is the {[(13C NMR peak area from 34.4 ppm to 34.6 ppm) divided by (the 13C NMR sum integral area from 160.0 to 100.0 and from 60.0 ppm to 0.00 ppm)]×100}, that is >0.010%, as determined by 13C NMR.

The Mooney Viscosity and the rheology properties of the ethylene/alpha-olefin/non-conjugated polyene interpolymer (V0.1, V100, V0.1/V100, tan delta (0.1 rad/s or 100 rad/s), each at 190° C.) is that of the neat interpolymer (no oil, no filler). The interpolymer may be stabilized with "ppm amounts" of one or more antioxidants and/or other stabilizers.

The inventive composition may comprise a combination of two or more embodiments described herein. The ethylene/alpha-olefin/non-conjugated polyene interpolymer may comprise a combination of two or more embodiments described herein.

In one embodiment, the ethylene/alpha-olefin/non-conjugated polyene interpolymer has a "13C NMR % iCB Peak Area," which is the {[(13C NMR peak area from 34.4 ppm to 34.6 ppm) divided by (the 13C NMR sum integral area from 160.0 to 100.0 and from 60.0 ppm to 0.00 ppm)]×100}, that is ≥0.012%, or ≥0.015%, or ≥0.020%, or ≥0.025%, as determined by 13C NMR. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a "13C NMR % iCB Peak Area," which is the {[(13C NMR peak area from 34.4 ppm to 34.6 ppm) divided by (the 13C NMR sum integral area from 160.0 to 100.0 and from 60.0 ppm to 0.00 ppm)]×100}, that is ≥0.030%, or ≥0.035%, or ≥0.040%, or ≥0.045%, or ≥0.050%, as determined by 13C NMR. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a "13C NMR % iCB Peak Area," which is the { [(13C NMR peak area from 34.4 ppm to 34.6 ppm) divided by the (the 13C NMR sum integral area from 160.0 to 100.0 and from 60.0 ppm to 0.00 ppm)]×100}, that is ≤0.500%, or ≤0.400%, or ≤0.300%, or ≤0.200%, as determined by 13C NMR. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a "13C NMR iCBI value ≥0.030, or ≥0.040, or ≥0.050, or ≥0.060, or ≥0.070, or ≥0.080, or ≥0.090, or ≥0.100, or ≥0.110, or ≥0.120, or ≥0.130, or ≥0.140, or ≥0.150, or ≥0.160, or ≥0.170, or ≥0.180, or ≥0.190, or ≥0.200, or ≥0.210, or ≥0.220, or ≥0.230, or ≥0.240 per 1000 carbons, as determined by 13C NMR, described herein. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a "13C NMR % Peak Area," which is the {[(13C NMR peak area from 21.3 ppm to 22.4 ppm) divided by (total integral area from 19.3 ppm to 22.4 ppm)]×100}, that is ≥3.5%, or ≥4.0%, or ≥4.5%, or ≥5.0%, or ≥5.5%, or ≥6.0%, or ≥6.5%, or ≥7.0%, or ≥7.5%, or ≥8.0%, or ≥8.5%, or ≥9.0%, or ≥10.0%, as determined by 13C NMR, described herein. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has an amount of intermediate branches (iCBI)>0.03 per 1000 carbons. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a Mooney Viscosity from 40 to 100, or from 50 to 100, or from 60 to 90 (ML 1+4, 125° C.). In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a weight average molecular weight Mw from 100,000 to 600,000 g/mole, or from 100,000 to 500,000 g/mole. In one embodiment, the ethylene/alpha-olefin/non-conjugated polyene interpolymer has a weight average molecular weight (Mw) from 110,000 to 550,000 g/mole, or from 120,000 to 500,000 g/mole, or from 130,000 to 450,000 g/mole, or from 140,000 to 400,000 g/mole. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a MWD from 2.00 to 3.20, of from 2.10 to 3.10, or from 2.20 to 2.90. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a Tan D/RR>−1.13E-06 (mole/g)×Mw+0.37; where Tan D is the tan delta at 0.1 rad/s, 190° C.; RR is the ratio of V0.1/V100 (190C); Mw is the weight average molecular weight as determined by conventional GPC.

In one embodiment, the ethylene/alpha-olefin/non-conjugated polyene interpolymer has a Tan D/RR>−1.13E-06 (mole/g)×Mw+0.41; where Tan D is the tan delta at 0.1 rad/s, 190C; RR is the ratio of V0.1/V100 (190C); Mw is the weight average molecular weight as determined by conventional GPC.

In one embodiment, the wherein the ethylene/alpha-olefin/non-conjugated polyene interpolymer has a Tan D/RR>−1.13E-06 (mole/g)×Mw+0.51; where Tan D is the tan delta at 0.1 rad/s, 190° C.; RR is the ratio of V0.1/V100 (190C); Mw is the weight average molecular weight as determined by conventional GPC.

In one embodiment, the ethylene/alpha-olefin/non-conjugated polyene has a viscosity at 0.1 rad/sec, 190° C., from 20,000 Pa·s to 1,200,000 Pa·s.

In one embodiment, the ethylene/alpha-olefin-/non-conjugated polyene interpolymer has a rheology ratio (V0.1/V100 at 190° C.) from 5 to 90.

In one embodiment, the ethylene/alpha-olefin/non-conjugated polyene interpolymer has a tan delta (0.1 rad/s, 190° C.) from 1.5 to 4.80, or from 1.60 to 4.20, or from 1.8 to 3.60. In a further embodiment, the interpolymer is an EAODM, and further an ethylene/propylene/-diene (EPDM) terpolymer. In a further embodiment, the diene is 5-ethylidene-2-norbornene (ENB).

In one embodiment, the composition comprises from 80 to 99 weight percent of the ethylene/alpha-olefin/non-conjugated polyene interpolymer, based on the sum weight of all polymer components of the composition. In one embodiment, the composition comprises from 80 to 99 weight percent of the ethylene/alpha-olefin/non-conjugated polyene interpolymer, based on the sum weight of the composition.

In one embodiment, the ethylene/alpha-olefin/non-conjugated polyene is an EPDM.

In one embodiment, the ethylene/alpha-olefin/non-conjugated polyene interpolymer has a viscosity at 0.1 rad/sec, 190° C., from 20,000 Pa·s to 1,500,000 Pa·s, or from 25,000 to 1,400,000 Pa·s, or from 30,000 to 1,300,000 Pa·s, or from 35,000 to 1,200,000 Pa·s, or from 40,000 to 1,200,000 Pa·s. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a rheology ratio (V0.1/V100 at 190° C.) from 5 to 75, or from 6 to 80, or from 7 to 85, or from 8 to 90. In a further embodiment, the interpolymer is an EAODM, and further an ethylene/propylene/diene (EPDM) terpolymer. In a further embodiment, the diene is 5-ethylidene-2-norbornene (ENB).

In one embodiment, the composition comprises from 80 to 98 weight percent of the ethylene/alpha-olefin/non-conjugated polyene interpolymer, based on the sum weight of all polymer components of the composition. In a further embodiment, the interpolymer is an EAODM, and further an ethylene/propylene/diene (EPDM) terpolymer. In a further embodiment, the diene is 5-ethylidene-2-norbornene (ENB).

In one embodiment, the composition comprises from 80 to 99 wt %, or from 85 to 99 wt %, or from 90 to 99 wt %, or from 95 to 99 wt %, or from 98 to 99 wt % of the ethylene/alpha-olefin/non-conjugated polyene interpolymer, based on the weight of the composition. In a further embodiment, the interpolymer is an EAODM, and further an ethylene/propylene/diene (EPDM) terpolymer. In a further embodiment, the diene is 5-ethylidene-2-norbornene (ENB).

In one embodiment, the composition comprises from 80 to 99 wt %, or from 85 to 99 wt %, or from 90 to 99 wt %, or from 95 to 99 wt %, or from 98 to 99 wt % of the ethylene/alpha-olefin/non-conjugated polyene interpolymer, based on sum weight of all polymer components of the composition. In a further embodiment, the interpolymer is an EAODM, and further an ethylene/propylene/diene (EPDM) terpolymer. In a further embodiment, the diene is 5-ethylidene-2-norbornene (ENB).

In one embodiment, the composition comprises from 10 to 50 wt %, or from 20 to 40 wt % of the ethylene/alpha-olefin/non-conjugated polyene interpolymer, based on the weight of the composition. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene interpolymer has a density from 0.850 to 0.890 g/cc, or from 0.855 to 0.890 g/cc, or from 0.860 to 0.890 g/cc. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/alpha-olefin/non-conjugated polyene is an EPDM. In a further embodiment, the interpolymer is an EAODM, and further an ethylene/propylene/-diene (EPDM) terpolymer. In a further embodiment, the diene is 5-ethylidene-2-norbornene (ENB).

In one embodiment, the ethylene/alpha-olefin/non-conjugated polyene interpolymer has a Mooney Viscosity greater than, or equal to, 30, further greater than, or equal to, 40 (ML 1+4, 125° C.). Mooney viscosity is that of the neat polymer (no oil, no filler). The polymer may be stabilized with "ppm amounts" of one or more antioxidants and/or other stabilizers.

In one embodiment, the ethylene/alpha-olefin/non-conjugated polyene interpolymer comprises from 50 to 90 weight percent ethylene, further from 55 to 85 weight percent ethylene, further from 60 to 80 weight percent ethylene, and further from 65 to 75 weight percent ethylene, based on the weight of the ethylene/alpha-olefin/non-conjugated polyene interpolymer. In a further embodiment, the interpolymer is an EAODM, and further an ethylene/propylene/diene (EPDM) terpolymer. In a further embodiment, the diene is 5-ethylidene-2-norbornene (ENB).

In one embodiment, the ethylene/α-olefin/non-conjugated polyene interpolymer is, independently, an ethylene/α-olefin/diene interpolymer (EAODM). In a further embodiment, the interpolymer is an ethylene/propylene/diene terpolymer (EPDM). In a further embodiment, the diene is 5-ethylidene-2-norbornene (ENB).

In one embodiment, the ethylene/α-olefin/non-conjugated polyene interpolymer comprises from 0.5 to 10.0 weight percent polyene, further from 1.0 to 8.0 weight percent polyene, and further from 1.5 to 6.0 weight percent polyene, based on the weight of the interpolymer. In a further embodiment, the polyene is a diene. In a further embodiment, the diene is 5-ethylidene-2-norbornene (ENB).

The first ethylene/α-olefin/non-conjugated polyene interpolymer, further an EAODM, and further an EPDM, may comprise a combination of two or more embodiments as described herein.

In one embodiment, the composition further comprises a crosslinking agent.

In one embodiment, the composition further comprises an oil.

In one embodiment, the composition further comprises a filler. Suitable fillers include, but are not limited to, clay, CaCO3, talc, carbon black, and mineral fibers. In one embodiment, the filler is present in an amount from 5 to 30 weight percent, based on the weight of the composition.

In one embodiment, an inventive composition further comprises at least one stabilizer. Suitable stabilizers include, but are not limited to, AO and UV stabilizers.

The inventive composition may comprise a combination of two or more embodiments described herein.

The invention also provides a crosslinked composition formed from an inventive composition of one or more embodiments described herein.

The invention also provides an article comprising at least one component formed from an inventive composition of one or more embodiments described herein. In a further embodiment, the article is selected from the group consisting of profiles, injection molded parts, gaskets, automotive parts, building and construction materials, shoe components, and tubes. In one embodiment, the article is an automotive part.

The invention also provides an article comprising at least one component formed from a crosslinked composition of one or more embodiments described herein. In a further embodiment, the article is selected from the group consisting of profiles, injection molded parts, gaskets, automotive parts, building and construction materials, shoe components, and tubes. An inventive article may comprise a combination of two or more embodiments described herein.

Also provided is a process to measure the amount of "Y-PE-type long chain branching per 1000 total carbons" in an ethylene/α-olefin/diene interpolymer; said process comprising at least the following:

a) dissolving the polymer in a solvent, to form a polymer solution;

b) analyzing the polymer solution using 13C NMR, at an analysis temperature from 20° C. to 200° C., and generating a 13C NMR spectrum; and wherein the polymer has a "Y-PE-type long chain branching" that has a signal for an alpha carbon (Y-PE$_\alpha$ signal) that has a peak maximum located in the range from 34.0 ppm to 35.0 ppm; and wherein the polymer has an amount of the "Y-PE-type long chain branching" ($A_{Y\text{-}PE}$) that is determined from the following Equation A:

$$A_{Y\text{-}PE} = (Y\text{-}PE_\alpha \text{ peak area})/3 \quad \text{(Eqn. A)},$$

wherein the "Y-PE$_\alpha$ peak area" is determined by integrating the area underneath the peak of the Y-PE$_\alpha$ signal located in the range from 34.0 ppm to 35.0 ppm; and wherein the amount of "Y-PE-type long chain branching per 1000 total carbons" is determined by integrating the area under the entire 13C NMR spectrum to obtain an area A, and then subtracting from A, the area of the "peak area due to solvent (S)", to obtain the "total peak area due to polymer (P)," and wherein the "Y-PE-type long chain branching per 1000 carbons" is determined from the following Equation B:

$$Y\text{-}PE\text{-type long chain branching per 1000 carbons} = (A_{Y\text{-}PE}/P) \times 1000 \text{ carbons} \quad \text{(Eqn. B)};$$

and wherein, the location of the Y-PE$_\alpha$ signal is determined by comparing the 13C NMR spectrum against a 13C NMR spectrum of a control polymer; and wherein the control polymer is an ethylene/1-octene copolymer that has a density from 0.910 to 0.930 g/cc and a melt index (I2) from 0.50 to 2.00 g/cc.

In one embodiment, for step b, the 13C NMR analysis uses a Pulse Delay=$\geq(5\times T1)$, where T1 is the spin-lattice relaxation time for the ethylene backbone.

In one embodiment, for step b, the 13C NMR analysis uses a cryoprobe. In a further embodiment, the probe is at a temperature $\geq 50°$ C., or $\geq 60°$ C., or $\geq 70°$ C., or $\geq 80°$ C., or $\geq 90°$ C., or $\geq 100°$ C., or $\geq 110°$ C., or $\geq 120°$ C. In another embodiment, the probe is at a temperature $\leq 160°$ C., or $\leq 150°$ C., or $\leq 140°$ C., or $\leq 135°$ C.

In one embodiment, for step a, a nitrogen purge is used during the sample dissolution.

In one embodiment, in step d), the polymer solution is analyzed using a cryoprobe.

In one embodiment, the polymer is an EPDM.

As used herein, the term "cryoprobe," refers to an NMR probe with an RF coil and a preamplifier that are both cooled with a cryogen (nitrogen gas and/or helium gas) to reduce electronic noise due to electrical resistance and other factors. This probe is also capable to run NMR at low temperatures (for example $\leq 25°$ C.) and high temperatures (for example $\geq 120°$ C.). For example, see "Z. Zhou, R. Kuemmerle, J. C. Stevens, D. Redwine, Y. He, X. Qiu, R. Cong, J. Klosin, N. Montañez, G. Roof, 13*C NMR of Polyolefins with a New High Temperature* 10 *mm Cryoprobe*, Journal of Magnetic Resonance, 2009, 200, 328."

In one embodiment, the solvent is a deuterated solvent. As used herein, the term "deuterated solvent," refers to an isotopologue of the solvent in which at least one hydrogen atom ("H") is replaced with a deuterium (heavy hydrogen) isotope ("D").

The 13C NMR process can be coupled, on or off line, with other analytical methods. For example, Gel Permeation Chromatography (GPC), Temperature Rising Elution Fractionation (TREF), Crystallization Elution Fractionation (CEF), or Thermal Gradient Interaction Chromatography (TGIC).

Ethylene/α-Olefin/Nonconjugated Polyenes Interpolymer

The ethylene/α-olefin/non-conjugated polyene interpolymers for the inventive compositions described herein, comprise, in polymerize form, ethylene, an α-olefin, and a non-conjugated polyene. Suitable examples of α-olefins include the C3-C20 α-olefins, further C3-C10 α-olefins, and preferably propylene. Suitable examples of non-conjugated polyenes include the C4-C40 non-conjugated dienes.

The α-olefin may be either an aliphatic or an aromatic compound. The α-olefin is preferably a C3-C20 aliphatic compound, preferably a C3-C16 aliphatic compound, and more preferably a C3-C10 aliphatic compound. Preferred C3-C10 aliphatic α-olefins are selected from the group consisting of propylene, 1-butene, 1-hexene and 1-octene, and more preferably propylene. In a further embodiment, the interpolymer is an ethylene/propylene/-diene (EPDM) terpolymer. In a further embodiment, the diene is 5-ethylidene-2-norbornene (ENB).

Illustrative non-conjugated polyenes include straight chain acyclic dienes, such as 1,4-hexadiene and 1,5-heptadiene; branched chain acyclic dienes, such as 5-methyl-1,4-hexadiene, 2-methyl-1,5-hexadiene, 6-methyl-1,5-heptadiene, 7-methyl-1,6-octadiene, 3,7-dimethyl-1,6-octadiene, 3,7-dimethyl-1,7-octadiene, 5,7-dimethyl-1,7-octadiene, 1,9-decadiene, and mixed isomers of dihydromyrcene; single ring alicyclic dienes such as 1,4-cyclohexadiene, 1,5-cyclooctadiene and 1,5-cyclododecadiene; multi-ring alicyclic fused and bridged ring dienes, such as tetrahydroindene, methyl tetrahydroindene; alkenyl, alkylidene, cycloalkenyl and cycloalkylidene norbornenes such as 5-methylene-2-norbornene (MNB), 5-ethylidene-2-norbornene (ENB), 5-vinyl-2-norbornene, 5-propenyl-2-norbornene, 5-isopropylidene-2-norbornene, 5-(4-cyclopentenyl)-2-norbornene, and 5-cyclohexylidene-2-norbornene. The polyene is preferably a nonconjugated diene selected from the group consisting of ENB, dicyclopentadiene, 1,4-hexadiene, 7-methyl-1,6-octadiene, and preferably, ENB, dicyclopentadiene and 1,4-hexadiene, more preferably ENB and dicyclopentadiene, and even more preferably ENB.

In one embodiment, the ethylene/α-olefin/non-conjugated polyene interpolymer, independently, comprises a majority amount of polymerized ethylene, based on the weight of the interpolymer. In a further embodiment, the ethylene/α-olefin/non-conjugated polyene interpolymer is an ethylene/α-olefin/dene interpolymer. In a further embodiment, the interpolymer is an EPDM. In a further embodiment, the diene is ENB.

In one embodiment, each ethylene/α-olefin/non-conjugated polyene interpolymer, independently, has a molecular weight distribution (Mw/Mn) from 2.00 to 3.00, further from 2.05 to 2.95, further from 2.10 to 2.90, further from 2.15 to 2.85. In a further embodiment, the ethylene/α-olefin/non-conjugated polyene interpolymer is an ethylene/α-olefin/dene interpolymer (EAODM). In a further embodiment, the interpolymer is an EPDM. In a further embodiment, the diene is ENB.

In one embodiment, the ethylene/α-olefin/non-conjugated polyene interpolymer has a Mooney viscosity, ML (1+4) at 125° C., $\leq 100$, or $\leq 90$, or $\leq 80$. In a further embodiment, the ethylene/α-olefin/non-conjugated polyene interpolymer is an ethylene/α-olefin/dene interpolymer. In a further embodiment, the interpolymer is an EPDM. In a further embodiment, the diene is ENB. In one embodiment, the ethylene/α-olefin/non-conjugated polyene interpolymer has a Mooney viscosity, ML (1+4) at 125° C., $\geq 20$, or $\geq 30$, or $\geq 40$. In a further embodiment, the ethylene/α-olefin/non-conjugated polyene interpolymer is an ethylene/α-olefin/dene interpolymer. In a further embodiment, the interpolymer is an EPDM. In a further embodiment, the diene is ENB. Mooney viscosity is that of the neat interpolymer. The neat polymer refers to the polymer without filler and without oil.

An ethylene/alpha-olefin/non-conjugated polyene interpolymer may comprise a combination of two or more embodiments as described herein. An ethylene/alpha-olefin/diene interpolymer may comprise a combination of two or more embodiments as described herein. An EPDM terpolymer may comprise a combination of two or more embodiments as described herein.

Crosslinking Agents

Crosslinking agents include, but are not limited to, sulfur-containing compounds, such as elemental sulfur, 4,4'-dithiodimorpholine, thiuram di- and polysulfides, alkylphenol disulfides, and 2-morpholino-dithiobenzothiazole; peroxides, such as di-tertbutyl peroxide, tertbutylcumyl peroxide, dicumyl peroxide, 2,5-dimethyl-2,5-di-(tertbutylperoxy) hexane, di-(tertbutylperoxyisopropyl) benzene, tertbutyl peroxybenzoate and 1,1-di-(tertbutylperoxy)-3,3,5-trimethylcyclohexane; metal oxides, such as zinc, magnesium, and lead oxides; dinitroso compounds, such as p-quinone-dioxime and p,p'-dibenzoylquinone-dioxime; and phenol-formaldehyde resins containing hydroxymethyl or halomethyl functional groups. The suitability of any of these vulcanizing agents for use in the invention will be largely governed by the choice of polymers, as is well known to those skilled in the compounding art. Sulfur can be a crystalline elemental sulfur or an amorphous elemental sulfur, and either type can be in pure form or supported on an inert carrier. An example of a supported sulfur is Rhenogran S-80 (80% S and 20% inert carrier) from Rhein Chemie.

In one embodiment of the invention, the sulfur containing compounds and the peroxides are the preferred crosslinking agents, and the sulfur containing compounds are most preferred. It is understood that mixtures of these vulcanizing agents can be employed, though this is generally not preferred. The amount of the vulcanizing agent can range from about 1 to 10 parts by weight, based upon 100 parts of the polymers in the composition. Vulcanization temperatures and time employed are typical. Temperatures ranging from about 250° F. to about 440° F., and times ranging from about one minute to about 120 minutes can be employed.

Additional crosslinking agents include, but are not limited to, phenolic resins, azides, aldehyde-amine reaction products, vinyl silanes, hydrosilylation, substituted ureas, substituted guanidines; substituted xanthates; substituted dithiocarbamates; and combinations thereof. See Encyclopedia of Chemical Technology, Vol. 17, 2nd edition, Interscience Publishers, 1968; also Organic Peroxides, Daniel Seem, Vol. 1, Wiley-Interscience, 1970), which are incorporated by reference herein in their entirety. The crosslinking agent may be a phenolic curing agent or a peroxide curing agent, with an optional co-agent, or hydrosilylation cross-linking agent with a hydrosilylation catalyst, or dibutyl tin dilaurate ("DBTDL"), with an optional co-agent alumina trihydrate ("ATH"), for silane-grafted interpolymer. A phenolic resin and $SnCl_2$ is used for EPDM curing (peroxide, or sulfur or hydrosilation curing systems can also be used). Suitable peroxides include, but are not limited to, aromatic dactyl peroxides; aliphatic dactyl peroxides; dibasic acid peroxides; ketene peroxides; alkyl peroxyesters; alkyl hydroperoxides (for example, diacetylperoxide; dibenzoylperoxide; bis-2,4-dichlorobenzoyl peroxide; di-tert-butyl peroxide; dicumylperoxode; tert-butyl-perbenzoate; tert-butylcumylperoxide; 2,5-bis (t-butylperoxy)-2,5-dimethylhexane; 2,5-bis (t-butylperoxy)-2,5-dimethylhexyne-3; 4,4,4',4'-tetra-(t-butylperoxy)-2,2-dicyclohexylpropane; 1,4-bis-(t-butylperoxyisopropyl)-benzene; 1,1-bis-(t-butylperoxy)-3,3,5-trimethyl-cyclohexane; lauroyl peroxide; succinic acid peroxide; cyclohexanone peroxide; t-butyl peracetate; butyl hydroperoxide; and the like. A crosslinking agent may comprise a combination of two or more embodiments as described herein.

Oils

Oils include, but are not limited to, petroleum oils, such as aromatic and naphthenic oils; polyalkylbenzene oils; organic acid monoesters, such as alkyl and alkoxyalkyl oleates and stearates; organic acid diesters, such as dialkyl, dialkoxyalkyl, and alkyl aryl phthalates, terephthalates, sebacates, adipates, and glutarates; glycol diesters, such as tri-, tetra-, and polyethylene glycol dialkanoates; trialkyl trimellitates; trialkyl, trialkoxyalkyl, alkyl diaryl, and triaryl phosphates; chlorinated paraffin oils; coumarone-indene resins; pine tars; vegetable oils, such as castor, tall, rapeseed, and soybean oils and esters and epoxidized derivatives thereof; and the like.

In one embodiment, the oil is present in an amount from 5 to 70 weight percent, further from 5 to 60 weight percent, further from 5 to 50 weight percent, based on the weight of the composition. In one embodiment, the oil is selected from the group consisting of nonaromatic oils, paraffinic oils, naphthenic oils, and combinations thereof. Suitable oils include, but are not limited to, SUNPAR 2280, PARALUX 6001, HYDROBRITE 550, and CALSOL 5550. An oil may comprise a combination of two or more embodiments as described herein.

Additives

An inventive composition may comprise one or more additional additives. Suitable additives include, but are not limited to, fillers, antioxidants and antiozonants, UV stabilizers, flame retardants, colorants or pigments, and combinations thereof. Fillers include, but are not limited to, carbon black, silicates of aluminum, magnesium, calcium, sodium, potassium and mixtures thereof; carbonates of calcium, magnesium and mixtures thereof; oxides of silicon, calcium, zinc, iron, titanium, and aluminum; sulfates of calcium, barium, and lead; alumina trihydrate; magnesium hydroxide; natural fibers, synthetic fibers, and the like. Some antioxidants and antiozonants include, but are not limited to, hindered phenols, bisphenols, and thiobisphenols; and substituted hydroquinones. Foaming agents, such as azodicarbonamide, can be used for making a foam structure.

In one embodiment, an inventive composition further comprises a thermoplastic polymer. Polymers, include, but not limited to, propylene-based polymers, ethylene-base polymers, and olefin multi-block interpolymers. Suitable ethylene-base polymers include, but are not limited to, high density polyethylene (HDPE), linear low density polyethylene (LLDPE), very low density polyethylene (VLDPE), ultra low density polyethylene (ULDPE), homogeneously branched linear ethylene polymers, and homogeneously branched substantially linear ethylene polymers (that is homogeneously branched long chain branched ethylene polymers).

Applications

The compositions of the present invention may be used to prepare a variety of articles or manufacture, or their component parts or portions. The inventive compositions may be converted into a finished article of manufacture by any one of a number of conventional processes and apparatus. Illustrative processes include, but are not limited to, extrusion, calendering, compression molding, and other typical thermoset material forming processes.

Articles include, but are not limited to, sheets, foams, molded goods, and extruded parts. Additional articles include automotive parts, weather strips, belts, hoses, building profiles, wire and cable jacketing, flooring materials, gaskets, tires and tire components, computer parts, building materials and footwear components. A skilled artisan can readily augment this list without undue experimentation.

Definitions

Unless stated to the contrary, implicit from the context, or customary in the art, all parts and percents are based on weight, and all test methods are current as of the filing date of this disclosure.

The term "composition," as used herein, includes the material(s), which comprise the composition, as well as reaction products and decomposition products formed from the materials of the composition. Any reaction product or decomposition product is typically present in trace or residual amounts.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure) and the term interpolymer as defined hereinafter. Trace amounts of impurities, such as catalyst residues, can be incorporated into and/or within the polymer. The term "interpolymer," as used herein, refers to polymers prepared by the polymerization of at least two different types of monomers. The term interpolymer thus includes the term copolymer (employed to refer to polymers prepared from two different types of monomers) and polymers prepared from more than two different types of monomers.

The term "ethylene-based polymer," as used herein, refers to a polymer that comprises, in polymerized form, a majority weight percent of ethylene (based on the weight of the polymer), and optionally may comprise one or more comonomers. The term "ethylene-based interpolymer," as used herein, refers to a polymer that comprises, in polymerized form, a majority weight percent of ethylene (based on the weight of the interpolymer), and at least one comonomer.

The term "ethylene/α-olefin/nonconjugated polyene interpolymer," as used herein, refers to a polymer that comprises, in polymerized form, ethylene, an α-olefin, and a nonconjugated polyene. In one embodiment, the "ethylene/α-olefin/nonconjugated polyene interpolymer" comprises a majority weight percent of ethylene (based on the weight of the interpolymer).

The term "ethylene/α-olefin/diene interpolymer," as used herein, refers to a polymer that comprises, in polymerized form, ethylene, an α-olefin, and a diene. In one embodiment, the "ethylene/α-olefin/diene interpolymer" comprises a majority weight percent of ethylene (based on the weight of the interpolymer).

The term, "ethylene/α-olefin copolymer," as used herein, refers to a copolymer that comprises, in polymerized form, a majority amount of ethylene monomer (based on the weight of the copolymer), and an α-olefin, as the only two monomer types.

The term, "propylene-based polymer," as used herein, refers to a polymer that comprises, in polymerized form, a majority amount of propylene monomer (based on the weight of the polymer), and optionally may comprise one or more comonomers.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

Test Methods

GPC (Conventional) for Mn. Mw, Mz, MWD and the LCBf of Polymer

A PolymerChar (Valencia, Spain) high temperature Gel Permeation Chromatography system consisting of an Infrared concentration/composition detector (IR-5), a PDI 2040 laser light scattering (Precision Detector, now Agilent) and a four capillary bridge viscometer (Viscotek, now Malvern) was used for MW and MWD determination. The carrier solvent was 1,2,4-trichlorobenzene (TCB). The solvent delivery pump, the on-line solvent degasser, autosampler, and column oven were from Agilent. The auto-sampler and detector compartments were operated at 160° C., and the column compartment was operated at 150° C. The columns were four PLgel Mixed-A LS, 20 micron columns (Agilent). The chromatographic solvent and the sample preparation solvent contained 250 ppm of butylated hydroxytoluene (BHT) and both solvent sources were nitrogen sparged. Polymer samples were prepared at targeted concentrations of 2 mg/mL by weighing samples via a computer controlled balance, and delivering calculated amount of solvent via an autosampler system. Samples were dissolved at 160° C. for 3 hour with gentle agitation. The injection volume was 200 μl, and the flow rate was 1.0 mL/minute.

Calibration of the GPC column set was performed with 21 narrow molecular weight distribution polystyrene standards. The molecular weights of the standards ranged from 580 to 8,400,000 g/mol, and were arranged in 6 "cocktail" mixtures, with at least a decade of separation between individual molecular weights. The polystyrene standard peak molecular weights were converted to polyethylene molecular weights using the following equation (as described in Williams and Ward, *J. Polym. Sci., Polym. Let.*, 6, 621 (1968)): $M_{PE}=A*(M_{PS})^B$ (Eq. 1), where M is the molecular weight, A has a cited value of 0.4316 and is further determined with a Dow internal reference with a known molecular weight, and B equals 1. A logarithmic molecular weight calibration is generated using a fifth-order polynomial fit as a function of elution volume. A flow rate marker of diluted decane in TCB was used to linearly correct the flow rate for all samples. Polystyrene standards were prepared in TCB at 1 mg/ml for molecular weights less than 1,000,000 and 0.5 mg/ml for molecular weight greater than 1,000,000 and left to swell overnight at room temperature. The heating time for the standards was 20 minutes prior to injection.

The mass detector constant, laser light scattering detector constant, and the viscometer detector constant were determined using a Dow internal reference with known value of the weight average molecular weight (120,000 g/mol, dn/dc=–0.104 mL/g) and intrinsic viscosity (1.873 dL/g). The chromatographic concentrations were assumed low enough to eliminate addressing 2nd Virial coefficient effects (concentration effects on molecular weight).

The Systematic Approach for the determination of detector offset was implemented in a manner consistent with that published by Balke, Mourey, et. al. (Mourey and Balke, *Chromatography Polym*. Chpt 12, (1992)) (Balke, Thitiratsakul, Lew, Cheung, Mourey, *Chromatography Polym*. Chpt 13, (1992)), using data obtained from the two detectors while analyzing the Dow reference of the broad linear polyethylene homopolymer (120,000 g/mol) and the narrow polystyrene standards. The Systematic Approach was used to optimize each detector offset to give molecular weight results as close as possible to those observed using the conventional GPC method.

The absolute weight average molecular weight Mw of samples, were characterized by the LS detector and IR-5 concentration detector using following equation:

$$Mw(\text{abs}) = K_{LS} * \frac{\sum(LS_i)}{\sum(IR_i)}, \quad \text{(Eq. 2)}$$

where, $\Sigma(LS_i)$ is the response area of LS detector, $\Sigma(IR_i)$ is the response area of IR-5 detector, and $K_{LS}$ is the instrument constant which was determined using the Dow internal reference with known concentration and the weight average molecular weight of 120,000 g/mol). The absolute molecular weight of each elution volume was calculated by following:

$$M_{LS,i} = K_{LS} * \frac{LS_i}{IR_i}. \quad \text{(Eq. 3)}$$

The intrinsic viscosity of samples, were characterized by the viscometer detector and IR-5 concentration detector using following equation:

$$IV_W = K_{IV} * \frac{\sum(DV_i)}{\sum(IR_i)}, \quad \text{(Eq. 4)}$$

where, $\Sigma(DV_i)$ is the response area of viscometer detector, $\Sigma(IR_i)$ is the response area of IR-5 detector, and $K_{IV}$ is the instrument constant which was determined using the Dow internal reference with known concentration and the intrinsic viscosity of 1.873 dL/g).

The intrinsic viscosity of each elution volume was calculated by following:

$$IV_i = K_{IV} * \frac{DV_i}{IR_i}. \quad \text{(Eq. 5)}$$

Elastomer resins were run with the Dow linear polyethylene reference, which was used as the linear reference to calculate g':

$$g'_i = (IV_{i,sample})/IV_{i,linearreference}) \quad \text{(Eq. 6)},$$

where the calculation utilizes the $IV_{i,linear\ reference}$ at equivalent absolute molecular weight in the linear reference sample. The $IV_{i,linear\ reference}$ slices are calculated from a fifth-order polynomial fit of the reference Mark-Houwink Plot.

The linear elastomer reference here was defined as elastomer with "exactly" the same amount of comonomers as in the resin characterized. The Mark-Houwink plot of this linear elastomer reference is parallel to a linear homopolyethylene (the same Dow internal reference) in the measured MW range, and overlap with the Mark-Houwink plot of the elastomer resin at the MWD peak position in this case. This process is considered as a "short chain branching (SCB) correction" for the elastomer in order to separate the g' change caused by short chain branching which refers to the comonomers in the elastomer. The SCB and SCB distribution along with MWD can be determined by using the composition mode of detector IR-5. The "SCB wt %" used here is an empirical value which could be consistent but may not be exactly equal to the comonomer weight fractions in the elastomer, especially when the there are multiple comonomers in the elastomer.

By introducing "SCB correction" on absolute molecular weight and intrinsic viscosity, the factor g' is decreased according to the determined by the empirical values of incorporation and thus the effect caused by comonomers was eliminated. Based on the comonomer level in each elastomer sample, the "SCB correction" could be different. This was accomplished by adjusting the value (either a single constant factor or a variable representing the distribution of comonomer incorporation as a function of molecular weight) of "SCB wt %" level.

The g' value of after "SCB correction" ($g_{LCB}'$) was converted to $g_{LCB}$ value, where $g_{LCB}$ is the Zimm-Stockmayer branching factor (B. H. Zimm and W. H. Stockmayer, J. Chem. Phys. 17, 1301, 1949) which is calculated using equation 7:

$$g'_{LCB} = g_{LBB}^\varepsilon \quad \text{(Eq. 7)},$$

where $\varepsilon$ has a value between 0.5-0.8 for most of polymers and the empirical value of 0.5 is used in this case.

The number of long chain branching in each polymer chain was calculated using equation 8 published by Zimm and Stockmayer:

$$g_{LCB} = \left[\left(1 + \frac{B_n}{7}\right)^{1/2} + \frac{4B_n}{9}\right]^{-1/2}, \quad \text{(Eq. 8)}$$

where $B_n$ is the number average branching per polymer chain. The value of $B_n$ is converted to long chain branching frequency (LCBf) value with a unit of per 1000 C, which a polymer chain consistent with 1000 saturated carbons which equals to a molecular weight of 14,000 g/mol.

FTIR Method for EPDM Composition Analysis for wt % C2, wt % ENB

The terpolymers containing ethylene, propylene, and 5-ethylidene-2-norbornene were analyzed using ASTM D3900 for its ethylene content, and ASTM D6047 for its ethylidene-norbornene or dicyclopentadiene content.

13C NMR Method for EPDM Composition Analysis—for the iCBI and Tacticity (% mm)

The samples were prepared by adding approximately "2.6 g" of a "50/50 mixture of tetrachloroethane-d2/orthodichlorobenzene" that is "0.025 M" in chromium acetylacetonate (relaxation agent) to "0.2 g sample" in a 10 mm NMR tube. The samples were dissolved, and homogenized, by heating the tube and its contents to 150° C. The data were collected using a Bruker 400 MHz spectrometer, equipped with a Bruker Dual DUL high-temperature CryoProbe. The data was acquired using "160 scans per data file," a six second pulse repetition delay, with a sample temperature of 120° C. The acquisition was carried out using a spectral width of 25,000 Hz and a file size of 32 K data points.

NMR spectral analysis of each composition of the examples was carried out using the following analysis method. Quantitation of monomers present in EPDM can also be calculated using the following equations (1 through 9). The calculation of moles ethylene normalizes the spectral range from 55.0 to 5.0 ppm to 1000 integral units. The contribution under the normalized integral area only accounts for 7 of the ENB carbons. The ENB diene peaks at 111 and 147 ppm are excluded from the calculation due to concerns that double bonds may react at high temperatures.

$$molesEth = \frac{(1000 - 3*molesP - 7*molesENB)}{2} \quad \text{Equation 1}$$

$$molesENB = CH3(13.6 - 14.7 \; ppm) \quad \text{Equation 2}$$

$$molesP = CH3(19.5 - 22.0 \; ppm) \quad \text{Equation 3}$$

$$\text{mole \% ethylene} = \frac{100*molesE}{molesE + molesP + molesENB} \quad \text{Equation 4}$$

$$\text{mole \% propylene} = \frac{100*molesP}{molesE + molesP + molesENB} \quad \text{Equation 5}$$

$$\text{mole \% ENB} = \frac{100*molesENB}{molesE + molesP + molesENB} \quad \text{Equation 6}$$

$$\text{Wt \% ethylene} = \frac{100*\text{mole \%} \; E*28}{\text{mole \%} \; E*\text{mole \%} \; P*42 + \text{mole \%} \; ENG*120} \quad \text{Equation 7}$$

$$\text{Wt \% propylene} = \frac{100*\text{mole \%} \; P*42}{\text{mole \%} \; E*28 - \text{mole \%} \; P*42 + \text{mole \%} \; ENB*120} \quad \text{Equation 8}$$

$$\text{Wt \% ENB} = \frac{100*\text{mole \%} \; ENB*120}{\text{mole \%} \; E*28 + \text{mole \%} \; P*42 + \text{mole \%} \; ENB*120} \quad \text{Equation 9}$$

Propylene Tacticity % mm Area 13C NMR

13C NMR spectral analysis of the EPDMs to quantitate the level of tacticity % mm was performed in a "50/50 mixture of tetrachloroethane-d2/orthodichlorobenzene", as described above. An NMR spectral analysis (see above) of the inventive EPDMs displayed a peak area from 21.3-22.4 ppm greater than 3.5% of the total integral area from 19.3 to 22.4 ppm. Similar spectral analysis of the comparative EPDMs showed less than 3.5% of the total integral area from 19.3 to 22.4 ppm. Spectral data were referenced to the EEE backbone at 30 ppm. Peak responses in this region typically are related to differences in propylene tacticity (% mm) that have been incorporated into the EPDM. A similar analysis can be done for another type of ethylene/α-olefin/nonconjugated polyene interpolymer.

Intermediate Chain Branching % Area 13C NMR

13C NMR spectral analysis of the EPDMs to quantitate the level of intermediate chain branching was performed using tetrachloroethane-d2 with 0.025 M chromium acetylacetonate, to improve the spectral resolution in the 34.6-34.4 ppm region. The samples were prepared by adding approximately "2.6 g" of a "tetrachloroethane-d2 with 0.025 M chromium acetylacetonate" to "0.3 g sample" in a 10 mm NMR tube. The samples were dissolved, and homogenized, by heating the tube and its contents to 140° C. The data were collected using a Bruker 400 MHz spectrometer with inverse gated NMR pulse, equipped with a Bruker Dual DUL high-temperature CryoProbe. The data was acquired using "8000 scans per data file," a 7.3 second pulse repetition delay, with a sample temperature of 120° C. Spectral data were referenced to the EEE backbone at 30 ppm.

Further 13C NMR spectral analysis of the inventive EPDMs displayed a methylene peak in the region from 34.4-34.6 ppm which is greater than 0.01% of the total integral area from 160.0 to 100.0 ppm plus 60.0 to 0.00 ppm (whole spectra excluding tetrachloroethane solvent). Similar spectral analysis of the comparative EPDMs showed less than 0.01% of the total integral area from 160.0 to 100.0 ppm plus 60.0 to 0.00 ppm (whole spectra excluding tetrachloroethane solvent). To convert the observed peak area from 34.6 ppm to 34.4 ppm to an intermediate chain branching index per 1000 carbons (iCBI), the area from 34.6 ppm to 34.4 ppm is multiplied by 3.33 to account for the three alpha carbons surrounding the branch (ten carbons divided by three alpha carbons). The inventive EPDMs displayed an iCBI of greater than 0.03 branches per 1000 carbons.

Dynamic Mechanical Spectroscopy (DMS)

Small angle oscillatory shear (melt DMS) was performed using a TA Instruments ARES, equipped with "25 mm parallel plates," under a nitrogen purge. The time between sample loading, and the beginning of the test, was set to five minutes for all samples. The experiments were performed at 190° C., over a frequency range of 0.1 to 100 rad/s. The strain amplitude was adjusted, based upon the response of the samples from 1 to 3%. The stress response was analyzed in terms of amplitude and phase, from which, the storage modulus (G'), loss modulus (G"), dynamic viscosity η*, and tan delta were calculated. Specimens for Dynamic Mechanical Spectroscopy were "25 mm diameter×3.3 mm thick" compression molded discs, formed at 180° C., and 10 MPa molding pressure, for five minutes, and then quenched between chilled platens (15-20° C.) for two minutes. The rheology properties (V0.1/V100 at 190° C.; also referred to as "RR", tan delta (0.1 rad/s, 190° C.) and tan delta (100 rad/s, 100° C.) were recorded.

Shore A Hardness

Hardness measurements were measured with a Shore A type durometer (ASTM D2240) with a five second delay. The durometer was placed onto a compression molded plaque, as described herein. Average of five measurements reported.

Mooney Viscosity

Mooney Viscosity (ML1+4 at 125° C.) was measured in accordance with ASTM 1646, with a one minute preheat time and a four minute rotor operation time. The instrument is an Alpha Technologies Mooney Viscometer 2000. The Mooney viscosity of each formulated compositions was measured using an uncured blanket (see experimental section), so that the viscosity of the uncured composition could be examined. Samples were conditioned for 24 hours at room temperature, prior to testing.

MDR Analysis (Cure Properties)

The cure kinetic profiles of each formulation at 160° C. and 180° C. were measured using an Alpha technology moving die rheometer (MDR) in accordance to ASTM D5289. Each test sample was prepared in accordance with ASTM D5289, Sections 7 and 8, using a sample cutting die from Alpha Technologies (model 2000R). The MDR Test was carried out at 160° C. and 180° C. over a period of 30 minutes. The rheology or curve of torque as a function of time for each formulated composition was measured from samples of uncured blanket, which was then cured during the MDR analysis. Samples were conditioned for 24 hours at room temperature, prior to testing. The visco-elastic properties, such as minimum S' torque (ML), maximum S' torque (MH), tan delta @ML, tan delta @MH, and time to reach a certain percentage of the cure state (for example, t95 corresponds to the time in minutes to reach the 95% state of cure), were measured during the cure cycle.

Compression Molded Plaques

The physical properties of the formulations were measured from vulcanized sheets, cured in a compression molder (for tensile, compression set testing, temperature retraction). Samples from the uncured blankets were cut, heated and cured in a compression molder to make test specimens in accordance with ASTM D3182, using a PHI (100 ton press). The desired mold (6 in.×6 in., or compression buttons) was placed on a platen. The sample (uncured blanket) was cut slightly smaller than the dimensions of the individual mold cavity. The mill direction was marked, and the sample was labeled. The mold was spray brushed with a dilute solution of silicone. The samples were in a preheated mold, taking care to place properly for mill direction. The platens were closed. The "normal" operating pressure was 100 tons, or as shown on the gauge as 200,000 pounds. When cure time ended, the bottom platen automatically opened. The samples were removed, and immediately placed in water to stop the curing. Samples were conditioned for 24 hours at room temperature, prior to testing. To cure (cure time) the samples, the samples were under minimum compression pressure of 3.5 MPa (500 psi) at 180° C. using t95 data (determined from MDR) plus three minutes for plaques, and using t95 (determined from MDR) data plus 15 minutes for compression set buttons.

Compression Set

Compression set was measured according to ASTM D395 at various temperatures. Compression set buttons of 29 mm (±0.5 mm) in diameter and 12.7 mm (±0.5 mm) thickness, were prepared as described under the section for compression molding. Each button sample was inspected for notches, uneven thickness and inhomogeneity, and selected buttons (without those defects) were tested. Compression set was performed on two specimens for each sample, at the temperatures specified, and the average results of the two specimens was reported. The button sample was placed in the compression device having two metal plates that could be pressed together, and locked into place at 75% of the original height of the button sample. The compression device, with the compressed samples, was then placed in an oven, and equilibrated at the appropriate temperature for a specified time (70 hrs for 23° C., 70° C. or 150° C.). In this test, the stress was released at the test temperature, and the thickness of the sample was measured after a 30 minute equilibration period at room temperature. Compression set is a measured of the degree of recovery of a sample following compression, and is calculated according to the equation $CS=(H0-H2)/(H0-H1)$; where H0 is the original thickness of the sample, H1 is the thickness of the spacer bar used, and H2 is the final thickness of the sample after removal of the compressive force. Average of three measurements reported.

Tensile Stress—Strain Properties

Tensile properties were measured using specimens which were die cut, using a small "dog bone" shaped micro tensile die, having the dimensions described in ASTM D-1708. Three die cut specimens were cut from the compression molded plaques, which were prepared as described under the Compression Molding section. Tensile properties (tensile strength and elongation) were measured at room temperature, following the method ASTM D-412, in the machine direction of an INSTRON MODEL 1122, made by INSTRU-MET. Average of three measurements reported.

Experimental

Continuous Polymerizations

In general terms, see U.S. Pat. Nos. 5,977,251 and 6,545,088, and the references therein. The polymer products are produced in a solution polymerization process using a continuously mixed loop reactor or using a CSTR.

Ethylene is introduced in a mixture of a solvent of ISOPAR E (a mixture of C8-C10 saturated hydrocarbons available from ExxonMobil), propylene and 5-ethylidene-2-norbornene (ENB), forming the reactor feed stream. Catalyst is fed to the reactor separately and activated in-situ using co-catalyst 1 and co-catalyst 2. The outlet of the reactor is consequently a mixture of polymer, solvent, and reduced levels of the initial monomer streams. The molecular weight of the polymer may be controlled by adjusting reactor temperature, monomer conversion and/or the addition of a chain terminating agent such as hydrogen. The polymerization reactions are performed under steady state conditions, that is, constant reactant concentration and continual input of solvent, monomers, and catalyst, and withdrawal of unreacted monomers, solvent and polymer. The reactor system is cooled and pressured to prevent formation of a vapor phase.

After polymerization, a small amount of water is introduced into the reactor exit stream as a catalyst kill, and the reactor exit stream is introduced into a flash vessel, in which the solids concentration is increased by at least 100 percent. A portion of the unreacted monomers, that is, ENB, ethylene, and propylene, and the unused diluent are then collected, and recycled back to the reactor feeds as appropriate.

Tables 1A and 1B outline the reaction conditions used to produce the inventive example 1, in a loop reactor. The reactor volume for the loop reactor is 30.6 gal. The polymer is collected and pelletized. Tables 2A and 2B include the reaction conditions to produce inventive example 2 in a CSTR reactor. Polymerization conditions are shown in Tables 1A, 1B, 2A and 2B.

Polymer properties of both inventive and comparative samples are shown in Table 3. It has been discovered that the inventive compositions have a unique combination of molecular weight, viscosity and rheological features. Such features are important for obtaining fine dispersion of the components added to a rubber formulation, such as carbon black, oils, curatives, talc, calcium carbonate, and other additives. Benefits are expected in the rubber mixing operations, and in the processing of final articles, such as extruded profiles, injection molded articles, rolled, calendared and compression molded articles. The inventive compositions comprise ethylene/alpha-olefin/non-conjugated polyene with a branching versus molecular weight relationship characteristic of linear rheology polymers as indicated by Tan D/RR>−1.13E-06*Mw+0.37, where Tan D is the Tan delta at 0.1 Rad/s at 190° C., RR is the rheology ratio V0.1/V100 at 190° C., and Mw is the weight average molecular weight.

TABLE 1A

EPDM Polymers - Loop Reactor

| Ex. EPDM | H2 (mol %)$^A$ Rx | C2 Conc. [g/L] Rx | Cat. Efficiency* [lb_poly/lb_metal]*10E6 Rx | Cat. Flow* [lb/hr] Cat. A or B* Rx | Cat. Solution Conc. (ppm) Rx | Cocat-1** Flow [lb/hr] Rx | Cocat-1 Solution Conc. [ppm] Rx | Cocat-2*** Flow [lb/hr] Rx | Cocat-2 Solution Conc. [ppm] Rx | Production Rate [lb/hr] Rx |
|---|---|---|---|---|---|---|---|---|---|---|
| Inv. 1 (CAT A) | 0.079 | 12.6 | 1.5 | 0.76 | 44.9 | 0.89 | 1000 | 0.6 | 498 | 51 |
| Comp A (CAT B) | 1.3 | 22.3 | 1.4 | 0.62 | 59.9 | 0.5 | 1000 | 0.34 | 498 | 50 |
| Comp B (CAT B) | 0.79 | 12.9 | 1 | 1.7 | 29.9 | 0.68 | 1000 | 0.47 | 498 | 51 |
| Comp C (CAT B) | 0.5 | 5 | 0.8 | 1.1 | 59.9 | 0.88 | 1000 | 0.6 | 498 | 52 |

*Catalyst A: [[6',6'''-((2R,4S)-pentane-2,4-diylbis(oxy))bis(3-(3,6-di-tert-butyl-9H-carbazol-9-yl)-3'-fluoro-5-(2,4,4-trimethylpentan-2-yl)-[1,1'-biphenyl]-2-ol)]] (2-)]-zirconium dimethyl. CatalystB: [[2',2'''-[1,3-propanediylbis(oxy-kO)]bis[3-[3,6-bis(1,1-dimethylethyl)-9H-carbazol-9-yl]-5'-fluoro-5-(1,1,3,3-tetramethylbutyl)[1,1'-biphenyl]-2-olato-kO]](2-)]-hafnium dimethyl.
**Cocatalyst-1 was a mixture of methyldi(C14-18 alkyl)ammonium salts of tetrakis(pentafluorophenyl)borate, prepared by reaction of a long chain trialkylamine (ARMEEN M2HT, available from Akzo-Nobel, Inc.), HCl and Li[B(C6F5)4], substantially as disclosed in U.S. Pat. No. 5,919,988 (Ex. 2). Cocatalyst-1 was purchased from Boulder Scientific, and used without further purification.
***Cocatalyst-2 (modified methylalumoxane (MMAO)) was purchased from Akzo Nobel, and used without further purification.
A: The mole % H2 is relative to the total reactant monomer feed to produce the polymer (C2, C3, ENB).

TABLE 1B

EPDM Polymers - Loop Reactor

| Ex. | Reactor Temp. [deg C.] Rx | Pressure [psig] Rx | Solvent Feed [lb/hr] Rx | Ethylene Feed [lb/hr] Rx | Propylene Feed [lb/hr] Rx | ENB Feed [lb/hr] Rx | % C2 Conversion Rx |
|---|---|---|---|---|---|---|---|
| Inv. 1 (CAT A) | 135 | 675 | 334 | 42.1 | 32.6 | 5.7 | 80.9 |
| Comp. A (CAT B) | 135 | 675 | 322.8 | 48.1 | 37.2 | 7.6 | 69.2 |
| Comp. B (CAT B) | 135 | 675 | 336.8 | 42 | 28 | 5.3 | 80.3 |
| Comp. C (CAT B) | 135 | 675 | 345.5 | 37.6 | 18.7 | 3.7 | 91.7 |

TABLE 2A

Process Conditions (CSTR (Rx))

| Inv. Ex. | H2 (mol %)$^A$ Rx | C2 Conc. [g/L] Rx | Catalyst Efficiency* [lb_poly/lb_metal] *10E6 Catalyst A Rx | Catalyst Flow* [lb/hr] Catalyst A* Rx | Catalyst Solution Conc. (ppm) Rx | Cocat-1** Flow [lb/hr] Rx | Cocat-1 Solution Conc. [ppm] Rx | Cocat-2*** Flow [lb/hr] Rx | Cocat-2 Solution Conc. [ppm] Rx | Production Rate [lb/hr] Rx |
|---|---|---|---|---|---|---|---|---|---|---|
| 2 | 0.019 | 19.99 | 2.95 | 0.37 A | 19.9 | 0.38 | 499.98 | 0.33 | 195.31 | 21.61 |

*Catalyst A: [[6',6'''-((2R,4S)-pentane-2,4-diylbis(oxy))bis(3-(3,6-di-tert-butyl-9H-carbazol-9-yl)-3'-fluoro-5-(2,4,4-trimethylpentan-2-yl)-[1,1'-biphenyl]-2-ol)]] (2-)]-zirconium dimethyl.
**Cocatalyst-1 was a mixture of methyldi(C14-18 alkyl)ammonium salts of tetrakis(pentafluorophenyl)borate, prepared by reaction of a long chain trialkylamine (ARMEEN M2HT, available from Akzo-Nobel, Inc.), HCl and Li[B(C6F5)4], substantially as disclosed in U.S. Pat. No. 5,919,988 (Ex. 2). Cocatalyst-1 was purchased from Boulder Scientific, and used without further purification.
***Cocatalyst-2 (modified methylalumoxane (MMAO)) was purchased from Akzo Nobel, and used without further purification.
A: The mole % H2 is relative to the total reactant monomer feed to produce the polymer (C2, C3, ENB).

TABLE 2B

Process Conditions (CSTR (Rx (R-600)))

| Inv. Ex. | Reactor Temp. [deg C.] Rx | Pressure [psig] Rx | Solvent Feed [lb/hr] Rx | Ethylene Feed [lb/hr] Rx | Propylene Feed [lb/hr] Rx | ENB Feed [lb/hr] Rx | % C2 Conversion Rx |
|---|---|---|---|---|---|---|---|
| 2 | 110.54 | 724.83 | 339.32 | 24.07 | 26.05 | 4.55 | 50.67 |

TABLE 3

Property Data for EPDM Polymers

| | Inv. 1 | Inv. 2 | Comp. A | Comp. B | Comp. C |
|---|---|---|---|---|---|
| Mooney Viscosity @ 125° C., MU | 70.3 | 200** | 69.5 | 68.7 | 68 |
| Ethylene wt % | 69.4 | 66.7 | 70.4 | 69.4 | 69.7 |
| ENB wt % | 5.10 | 3.47 | 5.00 | 5.00 | 4.80 |
| 13C NMR % iCB Peak Area* | 0.075 | 0.018 | ND | ND | ND |
| iCBI by NMR (branches/1000 C) | 0.250 | 0.060 | ND | ND | ND |
| LCBf by GPC (branches/1000 C) | 0.004 | 0.001 | 0.006 | 0.011 | 0.021 |
| Mn, g/mol | 68,551 | 198150 | 66,171 | 64,286 | 58,156 |
| Mw, g/mol | 167,265 | 431,966 | 164,767 | 164,571 | 162,838 |
| Mz, g/mol | 337,137 | 865114 | 330,193 | 331,186 | 352,004 |
| Mw/Mn | 2.44 | 2.18 | 2.49 | 2.56 | 2.8 |
| V0.1 (0.1 rad/s, 190° C.) Pa · s | 49,392 | 1129390 | 72,714 | 115,679 | 236,680 |
| V100 (100 rad/s, 190° C.) Pa · s | 4842 | 12956 | 4880 | 4487 | 4249 |
| RR V0.1/V100 | 10.2 | 87.2 | 14.9 | 25.8 | 55.7 |
| TanDelta @ 0.1 rad/s 190° C. | 3.27 | 1.80 | 1.99 | 1.29 | 0.82 |
| Propylene Tacticity % mm Area 13C NMR | 7.5 | 6.7 | 6.2 | 7.0 | 6.6 |
| TanD/RR | 0.321 | 0.021 | 0.134 | 0.050 | 0.015 |

*13C NMR % iCB Peak Area," which is the {[(13C NMR peak area from 34.4 ppm to 34.6 ppm) divided by (the 13C NMR sum integral area from 0.00 ppm to 60.0 ppm and from 160.0 ppm to 100.0 ppm)] × 100}, as determined by 13C NMR.
**Estimated Mooney Viscosity, based on the V100.
ND = Not Detected (<0.010).

TABLE 4

Property Data for Commercial Polymers (EPDM)

| | Mooney Viscosity (ML 1 + 4 @ 125° C.) | Ethylene (wt %) | ENB (wt %) | Mw (g/mol) | Mw/Mn | Low Shear Rheology (Pa · s; V0.1 @ 190° C.) | Rheology Ratio (V0.1/V100 @ 190° C.) | Tan delta @ 0.1 rad/s, 190° C. | TanD/RR |
|---|---|---|---|---|---|---|---|---|---|
| NORDEL 5565 | 65 | 50.47 | 7.75 | 181131 | 2.8 | 86735 | 24 | 1.5 | 0.0627 |
| NORDEL 4570 | 68 | 50.01 | 4.93 | 179700 | 2.6 | 105000 | 26 | 1.3 | 0.0508 |
| NORDEL 3745 | 45 | 70.11 | 0.53 | 135655 | 2.6 | 125000 | 38 | 1.1 | 0.0279 |
| NORDEL 4640 | 40 | 55.0 | 4.9 | 142668 | 2.8 | 44834 | 18 | 1.8 | 0.0991 |
| NORDEL 3760 | 64 | 67.13 | 2.28 | 167795 | 2.6 | 134000 | 30 | 1.1 | 0.0377 |
| K8570C | 80 | 66.0 | 5.0 | 206230 | 2.7 | 197000 | 39 | 0.9 | 0.0219 |
| Mitsui EPT3110M | 78 | 56.0 | 5.0 | 184770 | 2.6 | 173325 | 38 | 1.0 | 0.0274 |
| V6602 | 80 | 55.0 | 5.2 | 219090 | 2.6 | 148680 | 41 | 1.2 | 0.0288 |

13C NMR Analysis

An "NMR LCB" is typically defined as a chain having >six carbons and having the following structure, which is called Y-PE type LCB, as shown in Schematic A. In Schematic A, each "P notation" represents the respective remaining portion of the polymer molecule. Typically each "P" notation represents a different polymer structure, as compared to the other two "P" notations.

Schematic A: Y-PE type LCB

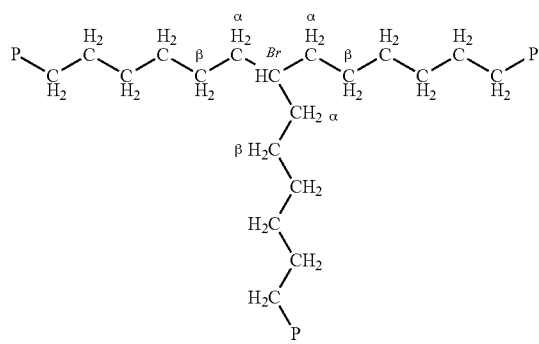

The solvents used in NMR analyses were commercially available, and used without further purification. For example 1,1,2,2-tetrachloroethane-d2 (TCE-d2) with purity D, 99.5% is available from Cambridge Isotope Laboratories, Inc. (CIL).

Table 5 lists some of the properties of the two EPDM polymers. Molecular weight information is from conventional GPC.

TABLE 5

Properties of two EPDM polymers

| Sample | Ethylene wt % | ENB wt % | Mooney (ML 1 + 4, T = 125° C.) | V0.1, Pa · s (190° C.) | RR** | Tan Delta (0.1 rad/s, 190° C.) | Mw, g/mol | Mw/Mn |
| --- | --- | --- | --- | --- | --- | --- | --- | --- |
| EPDM 1 | 69.2 | 4.6 | 69.8 | 49,392 | 10.2 | 3.27 | 167,265 | 2.44 |
| EPDM 2 | 68.8 | 4.2 | 65 | 236,680 | 55.7 | 0.82 | 162,838 | 2.8 |

*Each wt % based on the weight of the polymer.
**RR = rheology ratio = V0.1/V100 (each viscosity measured at 190° C.).

The control polymer is DOWLEX 2045G (ethylene/1-octene copolymer, density 0.9180-0.9220 g/cc, melt index (I2) 0.85-1.15 g/10 min, available from The Dow Chemical Company).

13C NMR—Analysis on Control Polymer

The polymer sample was prepared by adding approximately "2.6 g" of a "50/50 mixture of tetrachloroethane-d2/orthodichlorobenzene" that is "0.025 M" in chromium acetylacetonate (relaxation agent) to "0.2 g sample" in a 10 mm NMR tube, then the polymer solution was purged with nitrogen for 10 minutes. The sample was dissolved, and homogenized, by heating the tube and its contents to 140° C. The data were collected using a Bruker 400 MHz spectrometer, equipped with a Bruker Dual DUL high-temperature CryoProbe. The data was acquired using "320 scans per data file," with inverse gated decoupling (see Z. Thou, et al., "A new decoupling method for accurate quantification of polyethylene copolymer composition and triad sequence distribution with 13C NMR," Journal of Magnetic Resonance, 2007, 187, 225), a 7.3 second pulse repetition delay, with a sample temperature of 120° C. The acquisition was carried out using a spectral width of 25,000 Hz and a file size of 32 K data points. Relevant pecks from the respective 13C NMR spectra of the control polymer are shown in Table 6. The analysis took 0.5-1 hour.

Figure 2:
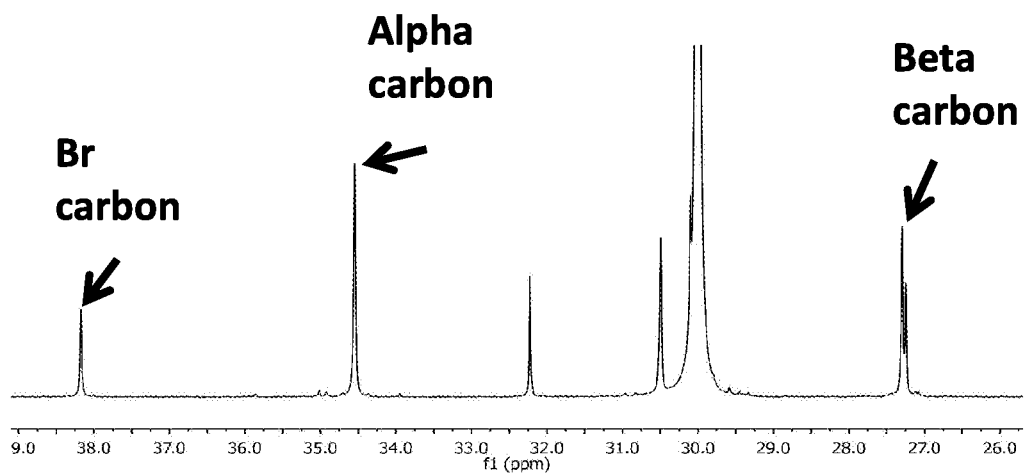
FIG. 2 is a 13C NMR spectrum of the control polymer (DOWLEX 2045G) in TCE-$d_2$/ODCB (50:50 w:w) at 120° C.

The 13C NMR spectrum is shown in FIG. 2. The Br carbon, alpha carbon and beta carbon in ethylene/1-octene copolymer have similar 13C NMR chemical shifts as Br carbon, alpha carbon and beta carbon in Y-PE type LCB have, and this sample is used as a reference to assign the LCB 13C NMR signals in the studies below.

TABLE 6

13C NMR Control Polymer

| Carbon | Control Polymer Chemical shift (ppm) |
| --- | --- |
| Br | 38.17 |
| alpha | 34.55 |
| beta | 27.29 |
| $(CH_2)_n$ = EEE* | 30.00 |

*ethylene backbone

13C NMR—Quantitative (EPDM 1, EPDM 2)

Each polymer sample was prepared by adding approximately "2.6 g of solvent (tetrachloroethane-d2 that has "0.025 M" in chromium acetylacetonate (relaxation agent))" to "0.3 g of polymer sample in a 10 mm NMR tube," and then purging the solution with polymer with nitrogen for 10 minutes. The samples were dissolved, and homogenized, by heating the tube, and its contents, to 140° C. The 13C NMR spectrum was collected using a BRUKER 400 MHz NMR spectrometer, equipped with a BRUKER Dual DUL high-temperature CryoProbe (see Z. Zhou, et al, J. Magn. Reson., 2009, 200, 328. [C&E News, 2009, 87, 37]).

The data was acquired using 8000 scans per data file with inverse gated decoupling (see Z. Zhou, et al., "A new decoupling method for accurate quantification of polyethylene copolymer composition and triad sequence distribution with 13C NMR," Journal of Magnetic Resonance, 2007, 187, 225). The pulse repetition delay was 7.3 seconds, and the analysis temperature was 120° C. The data acquisition was carried out using a spectral width of 25,000 Hz, and a file size of 32 K data points. Spectral data were referenced to the EEE backbone (ethylene backbone) at 30.0 ppm. Results are shown in Table 7. Each analysis took 16-17 hours.

EPDM 1 and EPDM 2 (Y-PE-Type LCB)

The chemical shift for Y-PEα is at 34.56 ppm, the chemical shifts for the solvent are 74.71 ppm, 74.43 ppm, and 74.16 ppm. The relevant integrated areas for EPDM 1 and EPDM 2 are shown in Table 7. Each area was determined using a commercial software MestReNova 10.0 (available from Mestrelab Research). For the integration of the peak area, vertical lines are drawn from the left of the peak to the right of the peak, and the area bounded between the peaks and the baseline is determined using the noted software. For example, see FIGS. 3 and 4.

TABLE 7

Peak Areas for each Noted Signal

|  | Y-PE$_\alpha$* | A$_{Y\text{-}PE}$ | Total spectrum (A) | Solvent (S) | Polymer (P) |
|---|---|---|---|---|---|
| EPDM 1 | 1.0 | 0.333 | 3194 | 1900 | 1294 |
| EPDM 2 | 1.0 | 0.333 | 39639 | 23649 | 15990 |

*Y-PE$_\alpha$ signal = LCB alpha signal.

Figure 3:
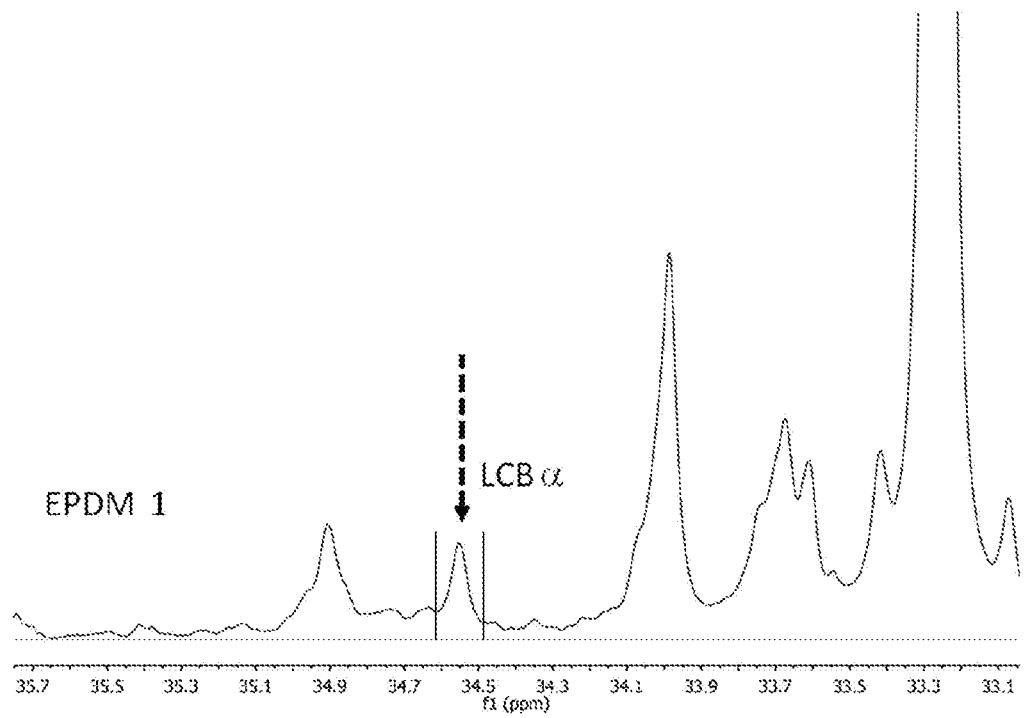
FIG. 3 is a 13C NMR spectrum of EPDM 1 in TCE-$d_2$ at 120° C.

The 13C NMR spectrum for EPDM 1 is shown in FIG. 3. Here A$_{Y\text{-}PE}$ is 0.333, P is 1294, and the LCB level is "0.257 LCB/1000 C," determined by using "Y-PE-type long chain branching per 1000 carbons"=[A$_{Y\text{-}PE}$/P]×1000 carbons (Equation B).

Figure 4:
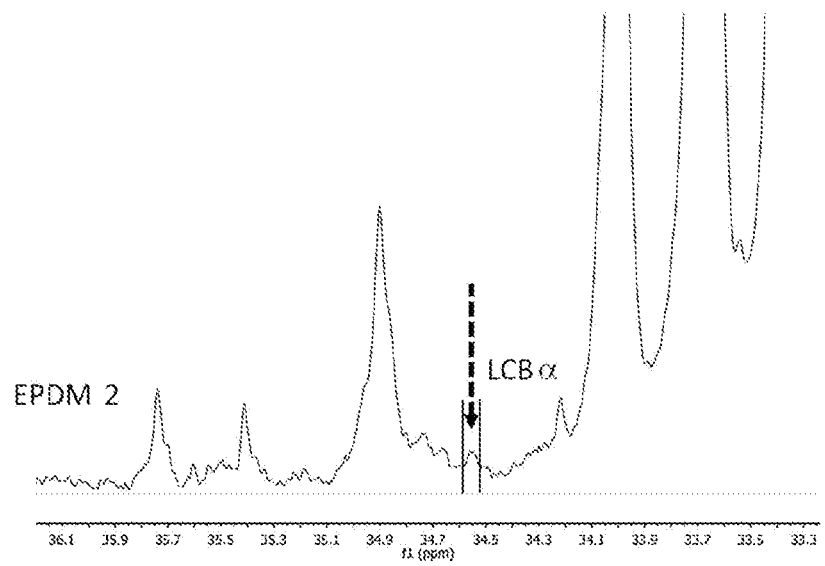
FIG. 4 is a 13C NMR spectrum of EPDM 2 in TCE-$d_2$ at 120° C.

The 13C NMR spectrum for EPDM 2 is shown in FIG. 4. Here A$_{Y\text{-}PE}$ is 0.333, P is 15990, LCB level is "0.021 LCB/1000 C," determined by using "Y-PE-type long chain branching per 1000 carbons"=[A$_{Y\text{-}PE}$/P]×1000 carbons (Equation B).

What is claimed is:

1. A composition comprising an ethylene/alpha-olefin/non-conjugated polyene interpolymer, and wherein the ethylene/alpha-olefin/non-conjugated polyene interpolymer comprises the following property: a "13C NMR % iCB Peak Area," which is the {[(13C NMR peak area from 34.4 ppm to 34.6 ppm) divided by (the 13C NMR sum integral area from 160.0 to 100.0 and from 60.0 ppm to 0.00 ppm)]×100}, that is >0.010%, as determined by 13C NMR; and
   wherein ethylene/alpha-olefin/non-conjugated polyene has "13C NMR % Peak Area" ≥4.0%, and wherein the "13C NMR % Peak Area" is the {[(13C NMR peak area from 21.3 ppm to 22.4 ppm) divided by (total integral area from 19.3 ppm to 22.4 ppm)]×100}.

2. The composition of claim 1, wherein the ethylene/alpha-olefin/nonconjugated polyene interpolymer has an amount of intermediate branches (iCB) >0.03 per 1000 carbons.

3. The composition of claim 1, wherein the ethylene/alpha-olefin/non-conjugated polyene interpolymer has a Mooney Viscosity from 40 to 100 (ML 1+4, 125° C.).

4. The composition of claim 1, wherein the ethylene/alpha-olefin/non-conjugated polyene interpolymer has a weight average molecular weight Mw from 100,000 to 500,000 g/mole.

5. The composition of claim 1, wherein the ethylene/alpha-olefin/non-conjugated polyene interpolymer has a MWD from 2.00 to 3.20.

6. The composition of claim 1, wherein the ethylene/alpha-olefin/non-conjugated polyene interpolymer has a Tan D/RR>−1.13E-06 (mole/g)×Mw+0.37; where Tan D is the tan delta at 0.1 rad/s, 190° C.; RR is the ratio of V0.1/V100 (190° C.); Mw is the weight average molecular weight as determined by conventional GPC.

7. The composition of claim 1, wherein the composition comprises from 80 to 99 weight percent of the ethylene/alpha-olefin/non-conjugated polyene interpolymer, based on the sum weight of all polymer components of the composition.

8. A crosslinked composition formed from the composition of claim 1.

9. An article comprising at least one component formed from the composition of claim 1.

10. A process to measure the amount of "Y-PE-type long chain branching per 1000 total carbons" in an ethylene/α-olefin/diene interpolymer; said process comprising at least the following:
   a) dissolving the polymer in a solvent, to form a polymer solution;
   b) analyzing the polymer solution using 13C NMR, at an analysis temperature from 20° C. to 200° C., and generating a 13C NMR spectrum; and
   wherein the polymer has a "Y-PE-type long chain branching" that has a signal for an alpha carbon (Y-PE$_\alpha$ signal) that has a peak maximum located in the range from 34.0 ppm to 35.0 ppm; and wherein the polymer has an amount of the "Y-PE-type long chain branching" (A$_{Y\text{-}PE}$) that is determined from the following Equation A:

$$A_{Y\text{-}PE} = (Y\text{-}PE_\alpha \text{ peak area})/3 \quad \text{(Eqn. A)},$$

wherein the "Y-PE$_\alpha$ peak area" is determined by integrating the area underneath the peak of the Y-PE$_\alpha$ signal located in the range from 34.0 ppm to 35.0 ppm; and
   wherein the amount of "Y-PE-type long chain branching per 1000 total carbons" is determined by integrating the area under the entire 13C NMR spectrum to obtain an area A, and then subtracting from A, the area of the "peak area due to solvent (S)", to obtain the "total peak area due to polymer (P)," and wherein the "Y-PE-type long chain branching per 1000 carbons" is determined from the following Equation B:

$$Y\text{-}PE\text{-type long chain branching per 1000 carbons} = (A_{Y\text{-}PE}/P) \times 1000 \text{ carbons} \quad \text{(Eqn. B)};$$

and
   wherein, the location of the Y-PE$_\alpha$ signal is determined by comparing the 13C NMR spectrum against a 13C NMR spectrum of a control polymer; and
   wherein the control polymer is an ethylene/1-octene copolymer that has a density from 0.910 to 0.930 g/cc and a melt index (I2) from 0.50 to 2.00 g/cc.

11. The composition of claim 1, wherein the ethylene/alpha-olefin/non-conjugated polyene interpolymer has "13C NMR % Peak Area"≥4.5%.

12. The composition of claim 1, wherein the ethylene/alpha-olefin/non-conjugated polyene interpolymer has "13C NMR % Peak Area"≥5.0%.

13. The composition of claim 1, wherein the ethylene/alpha-olefin/non-conjugated polyene interpolymer has "13C NMR % Peak Area"≥6.0%.

14. The composition of claim 1, wherein the ethylene/alpha-olefin/non-conjugated polyene interpolymer has a "13C NMR % iCB Peak Area,"≥0.015%.

15. The composition of claim 1, wherein the ethylene/alpha-olefin/non-conjugated polyene interpolymer has a "13C NMR % iCB Peak Area,"≥0.020%.

16. The composition of claim 1, wherein the ethylene/alpha-olefin/non-conjugated polyene interpolymer has a "13C NMR % iCB Peak Area,"≥0.050%.

17. The composition of claim 1, wherein the ethylene/alpha-olefin/non-conjugated polyene interpolymer has a 13C NMR iCBI value ≥0.050 per 1000 carbons.

18. The composition of claim 1, wherein the composition comprises from 80 to 99 wt % of the ethylene/alpha-olefin/non-conjugated polyene interpolymer, based on the weight of the composition.

19. The composition of claim 1, wherein the ethylene/alpha-olefin/non-conjugated polyene interpolymer has a tan delta (0.1 rad/s, 190° C.) from 1.5 to 4.80.

20. The composition of claim 1, wherein the ethylene/alpha-olefin/non-conjugated polyene interpolymer comprises from 65 to 75 weight percent ethylene, based on the weight of the interpolymer.

* * * * *